(12) United States Patent
Nauss

(10) Patent No.: US 10,779,699 B1
(45) Date of Patent: Sep. 22, 2020

(54) WIPE AND METHOD OF USE

(71) Applicant: Barry Richard Nauss, Harrisburg, PA (US)

(72) Inventor: Barry Richard Nauss, Harrisburg, PA (US)

( * ) Notice: Subject to any disclaimer, the term of this patent is extended or adjusted under 35 U.S.C. 154(b) by 1 day.

(21) Appl. No.: 16/240,716

(22) Filed: Jan. 5, 2019

(51) Int. Cl.
*A47L 13/16* (2006.01)
*A61K 8/02* (2006.01)
*A41D 13/08* (2006.01)

(52) U.S. Cl.
CPC ............ *A47L 13/16* (2013.01); *A41D 13/087* (2013.01); *A61K 8/0208* (2013.01); *A45D 2200/1018* (2013.01)

(58) Field of Classification Search
CPC ..... A47L 13/16; A47L 13/002; A41D 13/087; A61K 8/0208
See application file for complete search history.

(56) References Cited

U.S. PATENT DOCUMENTS

| | | | | |
|---|---|---|---|---|
| 2,058,213 A | * | 10/1936 | Cannonito | ............ A47L 13/022 15/229.13 |
| 4,014,616 A | * | 3/1977 | Mast, Jr. | ................ B65D 83/04 401/292 |
| 5,771,524 A | * | 6/1998 | Woods | ................... A45D 40/00 15/209.1 |

OTHER PUBLICATIONS

U.S. Appl. No. 29/677,865, Barry Richard Nauss.

* cited by examiner

*Primary Examiner* — Shay Karls
(74) *Attorney, Agent, or Firm* — Ted Masters

(57) ABSTRACT

A wipe is used with the thumb and at least one finger of one hand of a person. The wipe includes a shell which has a proximal end, a distal end, an outside surface, an inside surface, and an internal cavity. The shell is downwardly tapered from the proximal end to the distal end. The proximal end is open and includes a circular edge. The distal end is dome-shaped. The inside surface includes a ceiling at the distal end. A tab is connected to the ceiling, the tab projects toward the proximal end. The internal cavity is shaped and dimensioned to receive the thumb and at least one finger of the person with the tab disposed between the thumb and the at least one finger of the person.

15 Claims, 4 Drawing Sheets

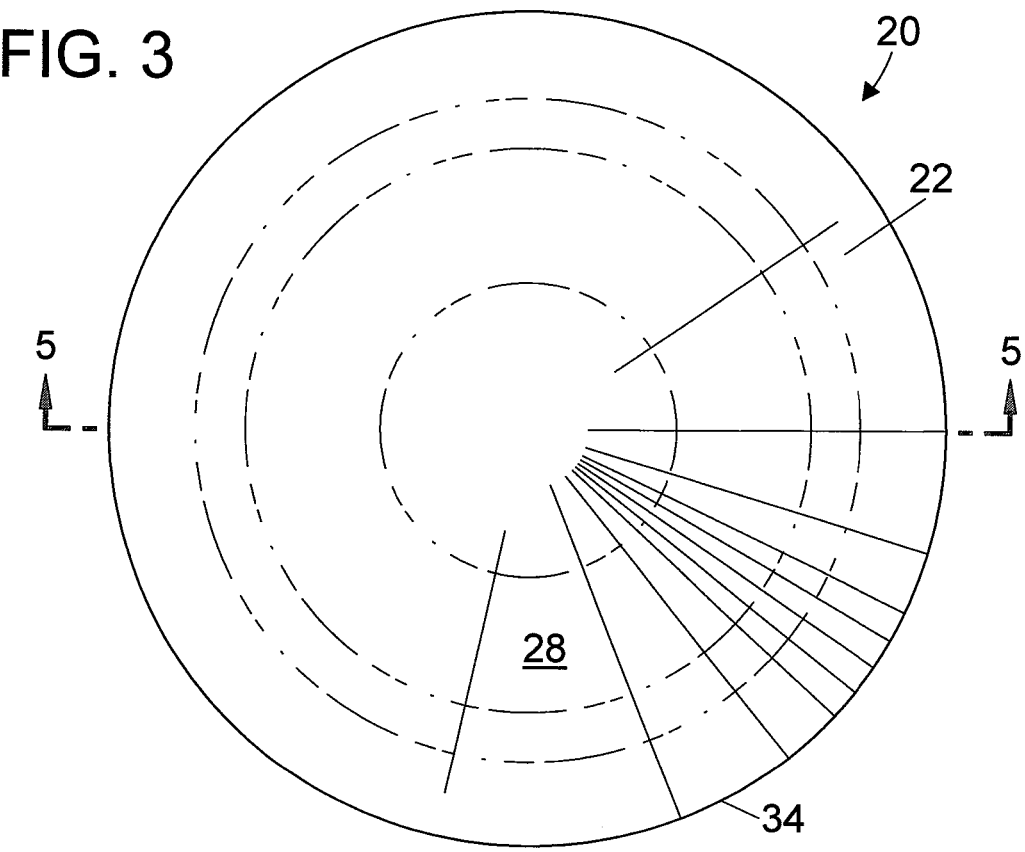
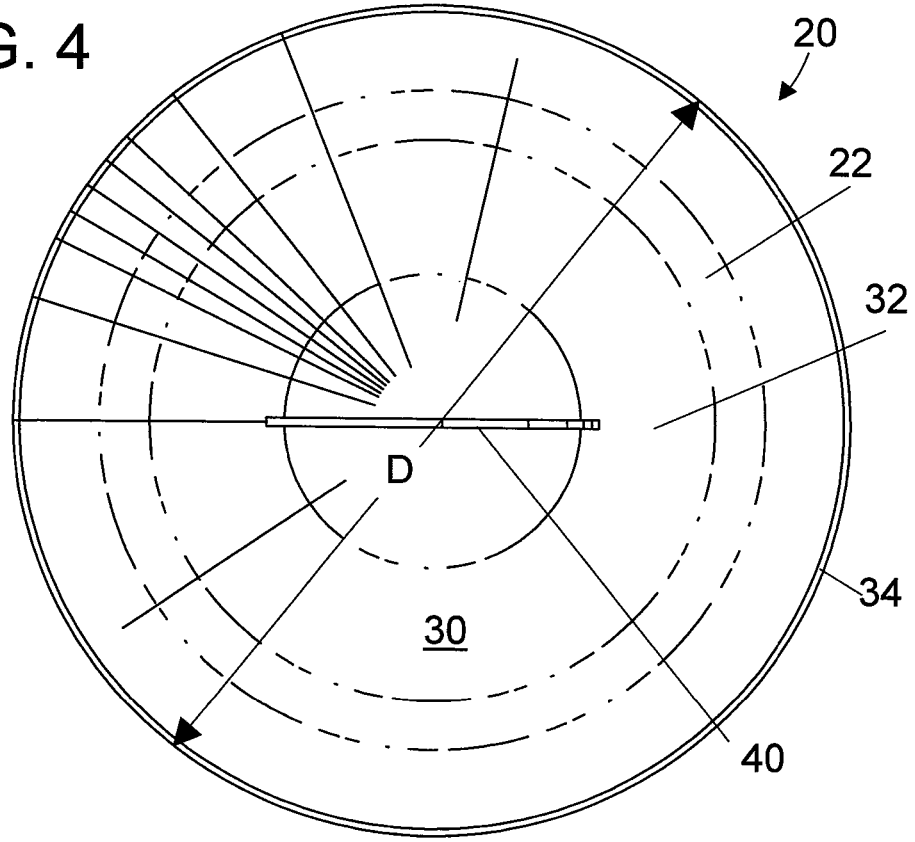

FIG. 8
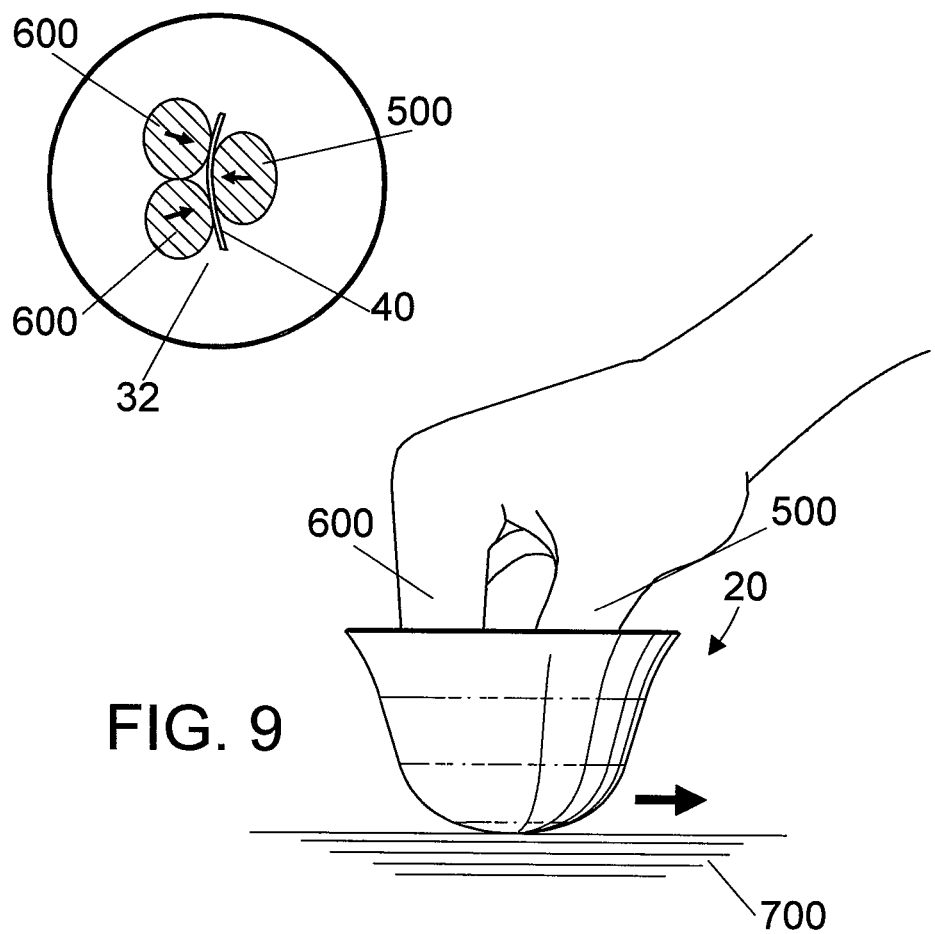
FIG. 9
FIG. 10
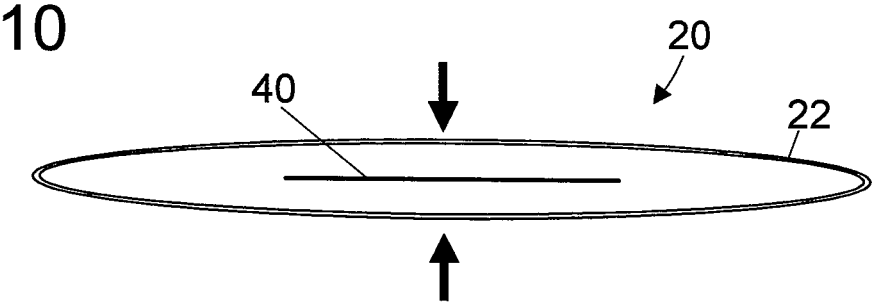

US 10,779,699 B1

WIPE AND METHOD OF USE

CROSS REFERENCE TO RELATED APPLICATION

None

TECHNICAL FIELD

The present invention pertains generally to wipes, and more particularly to a multipurpose wipe which is used by one hand of a person.

BACKGROUND OF THE INVENTION

Wipes are well known in the art. They are utilized to clean a surface by collecting and removing liquid or solid contaminants.

BRIEF SUMMARY OF THE INVENTION

The present invention is a multipurpose wipe which can be used in a variety of applications such as cosmetics, medical, toilet, baby wipes, general household cleaning, industrial applications, and the like. The wipe is designed to prevent direct contact between the user and the article which is being cleaned. The wipe includes an open proximal end which receives the thumb and at least one finger of the user. A tab is disposed inside the wipe at the distal end, and the user grips (pinches) the tab with the thumb and at least one finger. The wipe can be fabricated in various sizes depending upon the specific cleaning need.

In accordance with an embodiment, a wipe cooperates with the thumb and at least one finger of one hand of a person. The wipe includes a shell which has a proximal end, a distal end, an outside surface, an inside surface, and an internal cavity. The shell is downwardly tapered from the proximal end to the distal end. The proximal end is open and includes a circular edge. The distal end is dome-shaped. The inside surface includes a ceiling at the distal end. A tab is connected to the ceiling, the tab projects toward the proximal end. The internal cavity is shaped and dimensioned to receive the thumb and at least one finger of the person with the tab disposed between the thumb and the at least one finger of the person.

In accordance with another embodiment, the proximal end is flared.

In accordance with another embodiment, the shell has concave sides.

In accordance with another embodiment, the tab is shaped and dimensioned to be gripped by the thumb and the at least one finger of the person.

In accordance with another embodiment, the tab has a rounded edge.

In accordance with another embodiment, the shell has a height. The tab has a height which is less that half of the height of the shell.

In accordance with another embodiment, the shell is fabricated from a woven material.

In accordance with another embodiment, the wipe is fabricated from a non-woven material.

In accordance with another embodiment, the shell is positionable to a folded configuration in which two sides of the shell are parallel to the tab.

In accordance with another embodiment, the internal cavity is shaped and dimensioned to receive the thumb and exactly two fingers of the person with the tab disposed between the thumb and the exactly two fingers.

Other embodiments, in addition to the embodiments enumerated above, will become apparent from the following detailed description, taken in conjunction with the accompanying drawings, which illustrate, by way of example, the principles of the wipe and method of use.

BRIEF DESCRIPTION OF THE DRAWINGS

FIG. 3 is a top plan view of the wipe;
FIG. 4 is a bottom plan view of the wipe;
FIG. 8 is a cross sectional view along the line 8-8 of FIG. 7;
FIG. 9 is a side elevation view of the wipe being used by the person; and,
FIG. 10 is a bottom plan view of the wipe in a folded configuration.

DETAILED DESCRIPTION OF THE INVENTION

Figure 1:
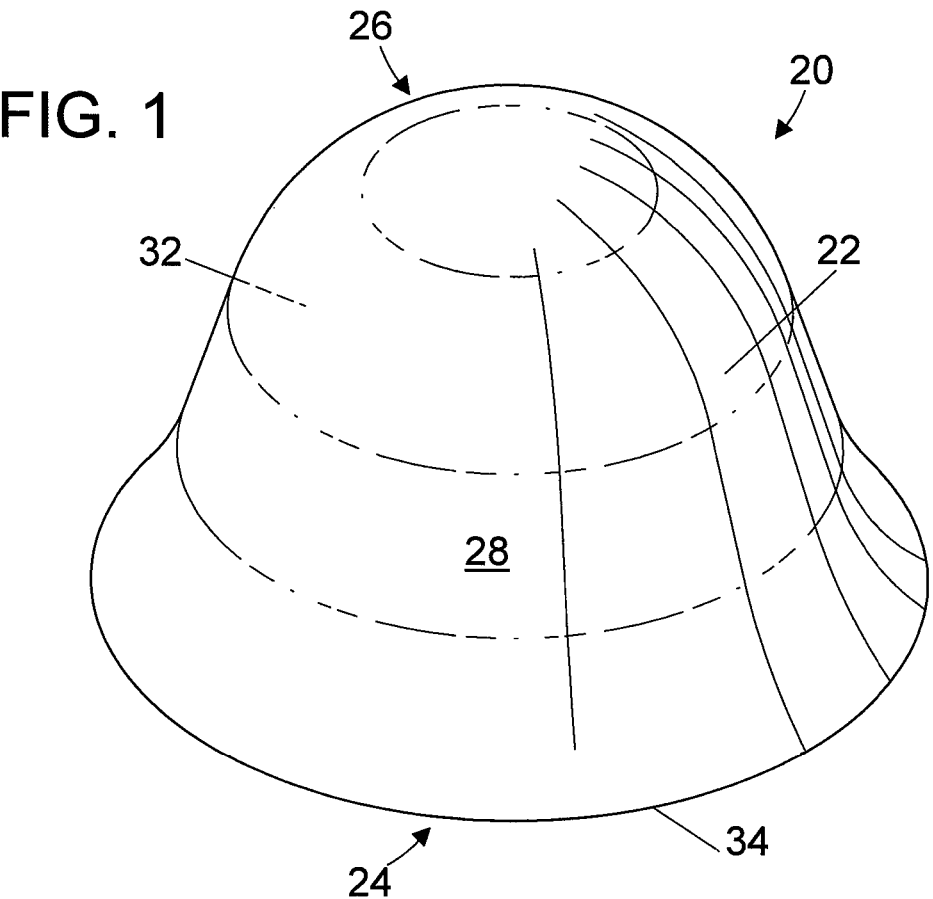
FIG. 1 is a perspective view of a wipe.
Figure 2:
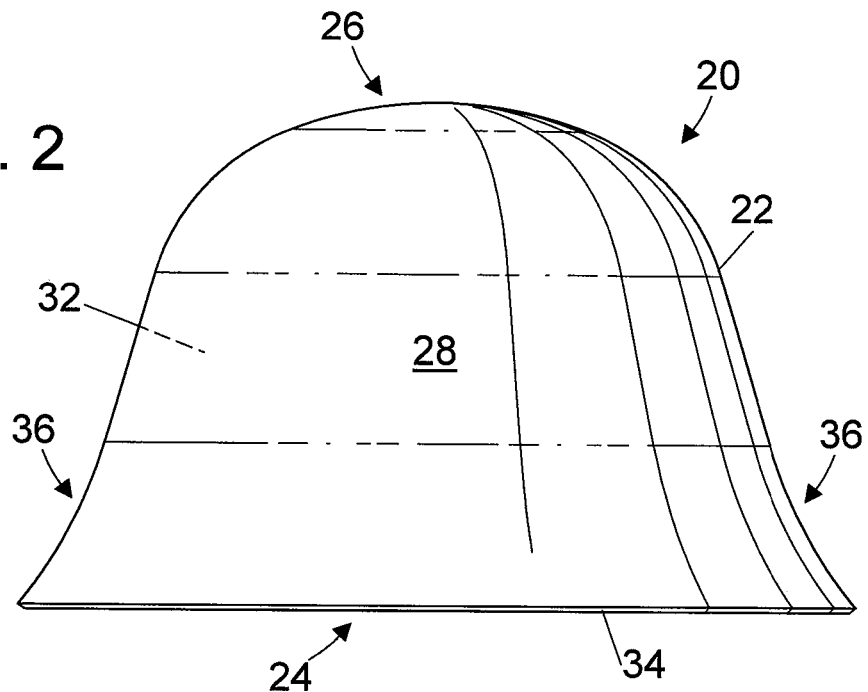
FIG. 2 is a side elevation view of the wipe.

Referring initially to FIGS. 1-5, there are illustrated perspective, side elevation, top plan, bottom plan, and cross sectional views respectively of a wipe generally designated as 20. Wipe 20 cooperates with (is used by) the thumb 500 and at least one finger 600 of one hand of a person (also refer to FIGS. 6-9). Wipe 20 includes a shell 22 which has a proximal end 24, a distal end 26, an outside surface 28, an inside surface 30, and an internal cavity 32. Proximal end 24 is open, includes a circular edge 34, and is shaped and dimensioned to receive the thumb 500 and finger(s) 600 of the hand of the person (also refer to FIGS. 6-9). Distal end 26 is dome-shaped. That is, distal end 26 comprises a 360° rounded structure. When viewed from the side as in FIG. 2, shell 22 has a bell shape which is downwardly tapered from proximal end 24 to distal end 26. That is, proximal end 24 is larger than distal end 26. The taper facilitates the use of wipe 20 by individuals having different size thumbs 500 and finger(s) 600. In FIG. 2 it is noted that proximal end 24 is flared which results in shell 22 having concave sides 36. The flare further facilitates use by individuals with different size thumbs and fingers(s). Wipe 20 can be fabricated in various sizes. In one embodiment circular edge 34 of proximal end 24 has a diameter of between about 2 inches and about 5 inches. It is noted in FIGS. 3 and 4 that shell 22 is circular in shape. In one embodiment this circular shape is the before use shape. In this embodiment shell 22 is fabricated from a material which has sufficient rigidity to hold the circular shape.

Figure 5:
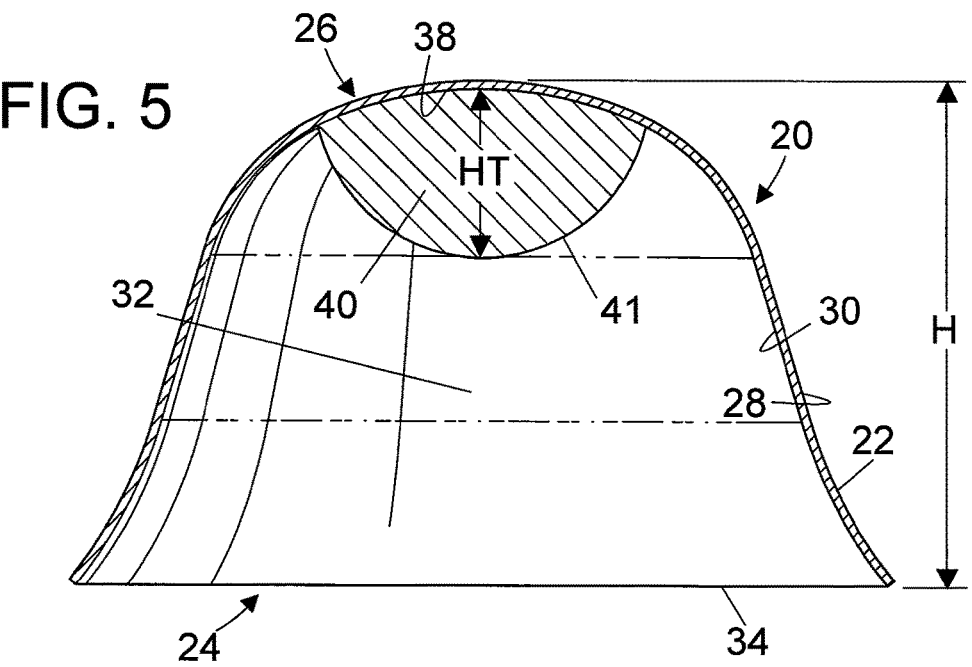
FIG. 5 is a cross sectional view along the line 5-5 of FIG. 3.

Referring to FIGS. 4 and 5, inside surface 30 includes a ceiling 38 at distal end 26. A tab 40 is connected to ceiling 38, and tab 40 projects toward proximal end 24. Internal cavity 32 is shaped and dimensioned to receive the thumb 500 and at least one finger 600 of the person with tab 40 disposed between the thumb 500 and the at least one finger 600 of the person (also refer to FIGS. 7 and 8). It is noted that cavity 32 is empty except for tab 40. It is also noted in FIG. 5 that tab 40 has a rounded (semicircular) edge 41. And that in an embodiment, shell 22 has a height H. Tab 40 has a height HT which is less that half of height H of shell 22.

Figure 6:
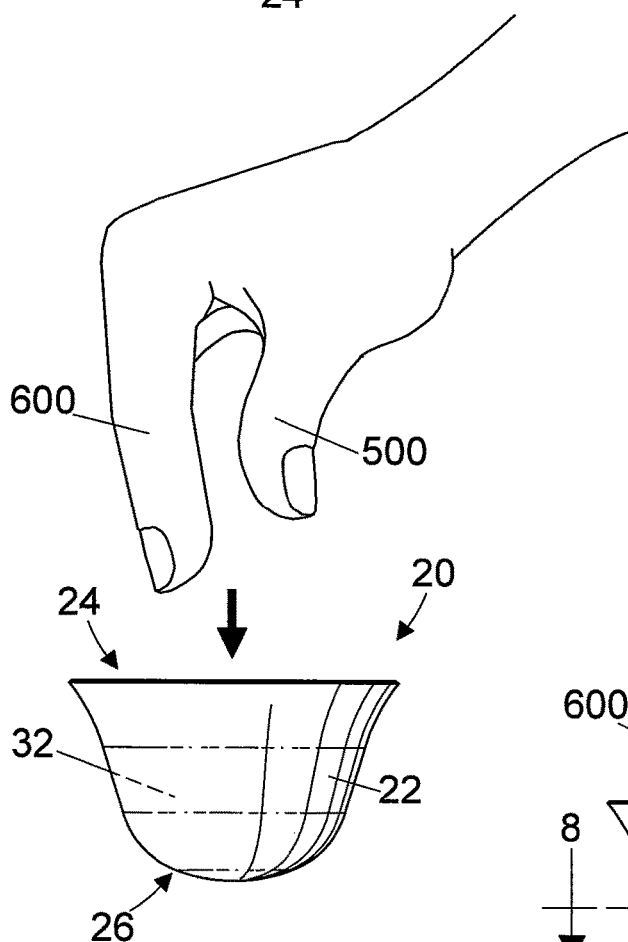
FIG. 6 is a reduced side elevation view of a person preparing to use the wipe.
Figure 7:
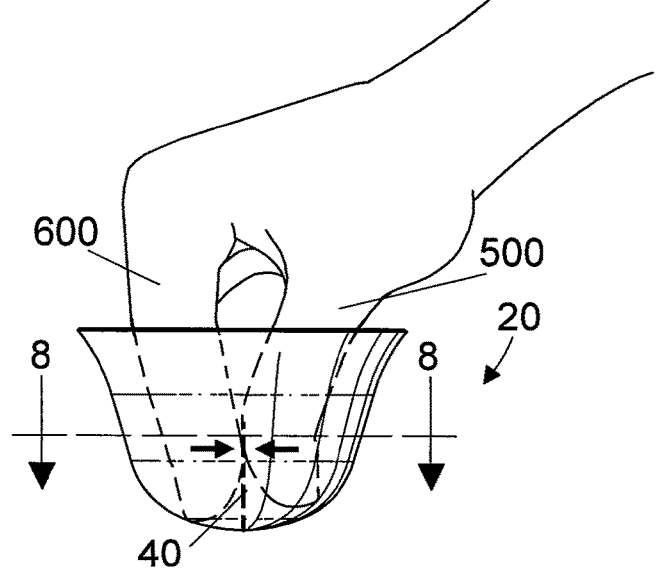
FIG. 7 is a reduced side elevation view of the person using at least one finger and the thumb of one hand to grip a tab.

FIG. 6 is a reduced side elevation view of a person preparing to use wipe 20, FIG. 7 is a reduced side elevation view of the person using at least one finger 600 and the thumb 500 of one hand to grip tab 40, and FIG. 8 is FIG. 8 is a cross sectional view along the line 8-8 of FIG. 7. In FIG. 6 the person moves thumb 500 and at least one finger 600 toward the open proximal end 24 of shell 22. In FIG. 7, the thumb 500 and finger(s) 600 are inserted into cavity 32 and used to grip tab 40 therebetween (refer to FIG. 8). This gripping provides the person with a firm hold while wipe 20 is being used. It is noted that tab 40 is shaped and dimensioned to be gripped by the thumb 500 and the at least one finger 600 of the person. In the shown embodiment of FIG. 8, tab 40 is gripped by thumb 500 and exactly two fingers 600. The number of fingers 600 used to grip tab 40 can vary as a function of both the size of wipe 20 and the specific use of wipe 20. For example for cosmetic use it may be advantageous to use one or two fingers, while for large surface cleaning applications a larger number of fingers would be more appropriate. Referring to FIG. 8, in one embodiment, internal cavity 30 is shaped and dimensioned to receive the thumb 500 and exactly two fingers 600 of the person with tab 40 disposed between the thumb 500 and the exactly two fingers 600.

FIG. 9 is a side elevation view of wipe 20 being used by the person with thumb 500 and at least one finger 600. In this instance wipe 20 is being used to clean a surface 700 such as a counter top.

FIG. 10 is a bottom plan view of wipe 20 in a folded configuration, such as could be used for pre-use packaging. The folded configuration is semi-flat wherein two sides of shell 22 are are parallel to tab 40.

Shell 22 can be fabricated for either woven or non-woven material. In one embodiment shell 22 is fabricated from paper, and in another embodiment shell 22 is fabricated from cloth. And as was previously pointed out, in an embodiment the material is of sufficient rigidity so that shell 22 holds the circular shape shown in FIGS. 1-5.

In terms of use, a method of wiping by using the thumb and at least one finger of one had of a person includes;
  (a) providing a wipe 20 including:
    a shell 22 having a proximal end 24, a distal end 26, an outside surface 28, an inside surface 30, and an internal cavity 32;
    the shell 22 being downwardly tapered from the proximal end 24 to the distal end 26;
    the proximal end 24 being open and including a circular edge 34;
    the distal end 26 being dome-shaped;
    the inside surface 30 including a ceiling 36 at the distal end 26;
    a tab 40 connected to the ceiling 36, the tab 40 projecting toward the proximal end 24; and,
    the internal cavity 30 shaped and dimensioned to receive the thumb 500 and at least one finger 600 of the person with the tab 40 disposed between the thumb 500 and the at least one finger 600 of the person;
  (b) inserting the thumb 500 and the at least one finger 600 into the cavity and gripping the tab 40 with the thumb 500 and the at least one finger 600; and,
  (c) using the wipe 20.
The wiping method further including;
  in (a), the internal cavity 32 shaped and dimensioned to receive the thumb 500 and exactly two fingers 600 of the person with the tab 40 disposed between the thumb 500 and the exactly two fingers 600; and,
  in (b), inserting the thumb 500 and exactly two fingers 600 into the cavity 32 and gripping the tab 40 with the thumb 500 and the exactly two fingers 600.

The embodiments of the wipe and method of use described herein are exemplary and numerous modifications, combinations, variations, and rearrangements can be readily envisioned to achieve an equivalent result, all of which are intended to be embraced within the scope of the appended claims. Further, nothing in the above-provided discussions of the wipe and method should be construed as limiting the invention to a particular embodiment or combination of embodiments. The scope of the invention is defined by the appended claims.

I claim:

1. A wipe, the wipe cooperating with the thumb and at least one finger of one hand of a person, the wipe comprising:
  a shell having a proximal end, a distal end, an outside surface, an inside surface, and an internal cavity;
  said shell being downwardly tapered from said proximal end to said distal end;
  said proximal end being open and including a circular edge;
  said proximal end being outwardly curved;
  said distal end being dome-shaped;
  said inside surface including a ceiling at said distal end;
  a tab connected to said ceiling, said tab projecting toward said proximal end, said tab being a thin partition; and,
  said internal cavity shaped and dimensioned to receive the thumb and at least one finger of the person with said tab disposed between the thumb and the at least one finger of the person.

2. The wipe according to claim 1, further including:
  said tab shaped and dimensioned to be gripped by the thumb and the at least one finger of the person.

3. The wipe according to claim 1, further including
  said shell having a height; and,
  said tab having a height which is less that half of said height of said shell.

4. The wipe according to claim 1, further including:
  said shell fabricated from a woven material.

5. The wipe according claim 1, further including:
  said wipe fabricated from a non-woven material.

6. The wipe according to claim 1, further including:
  said shell positionable to a folded configuration in which two sides of said shell are parallel to said tab.

7. The wipe according to claim 1, further including;
  said internal cavity shaped and dimensioned to receive the thumb and exactly two fingers of the person with said tab disposed between the thumb and the exactly two fingers.

8. The wipe according to claim 1, further including:
  said tab having a uniform thickness;
  said shell having concave external sides;
  said tab shaped and dimensioned to be gripped by the thumb and the at least one finger of the person;
  said tab having a rounded edge;
  said shell having a height;
  said tab having a height which is less that half of said height of said shell;
  said shell positionable to a folded configuration in which two sides of said shell are parallel to said tab; and,
  said shell fabricated from paper.

9. A wipe, the wipe cooperating with the thumb and at least one finger of one hand of a person, the wipe comprising:
- a shell having a proximal end, a distal end, an outside surface, an inside surface, and an internal cavity;
- said shell being downwardly tapered from said proximal end to said distal end;
- said proximal end being open and including a circular edge;
- said distal end being dome-shaped;
- said inside surface including a ceiling at said distal end;
- a tab connected to said ceiling, said tab projecting toward said proximal end, said tab being a thin partition;
- said internal cavity shaped and dimensioned to receive the thumb and at least one finger of the person with said tab disposed between the thumb and the at least one finger of the person; and,
- said tab having a uniform thickness.

10. A wipe, the wipe cooperating with the thumb and at least one finger of one hand of a person, the wipe comprising:
- a shell having a proximal end, a distal end, an outside surface, an inside surface, and an internal cavity;
- said shell being downwardly tapered from said proximal end to said distal end;
- said proximal end being open and including a circular edge;
- said distal end being dome-shaped;
- said inside surface including a ceiling at said distal end;
- a tab connected to said ceiling, said tab projecting toward said proximal end, said tab being a thin partition;
- said internal cavity shaped and dimensioned to receive the thumb and at least one finger of the person with said tab disposed between the thumb and the at least one finger of the person; and,
- said shell having concave external sides.

11. A method of wiping by using the thumb and at least one finger of one had of a person, comprising;
- (a) providing a wipe including:
  - a shell having a proximal end, a distal end, an outside surface, an inside surface, and an internal cavity;
  - said shell being downwardly tapered from said proximal end to said distal end;
  - said proximal end being outwardly curved;
  - said distal end being dome-shaped;
  - said inside surface including a ceiling at said distal end;
  - a tab connected to said ceiling, said tab projecting toward said proximal end, said tab being a thin partition; and,
  - said internal cavity shaped and dimensioned to receive the thumb and at least one finger of the person with said tab disposed between the thumb and the at least one finger of the person;
- (b) inserting the thumb and the at least one finger into said cavity and gripping said tab with the thumb and the at least one finger; and,
- (c) using said wipe.

12. The wiping method of claim 11, further including;
- in (a), said internal cavity shaped and dimensioned to receive the thumb and exactly two fingers of the person with said tab disposed between the thumb and the exactly two fingers; and,
- in (b), inserting the thumb and exactly two fingers into said cavity and gripping said tab with the thumb and the exactly two fingers.

13. The wiping method of claim 11 further including:
- in (a), said tab having a uniform thickness.

14. A wipe, the wipe cooperating with the thumb and at least one finger of one hand of a person, the wipe comprising:
- a shell having a proximal end, a distal end, an outside surface, an inside surface, and an internal cavity, said shell fabricated from paper;
- said shell being downwardly tapered from said proximal end to said distal end;
- said proximal end being open and including a circular edge;
- said distal end being dome-shaped;
- said inside surface including a ceiling at said distal end;
- a tab connected to said ceiling, said tab projecting toward said proximal end;
- said tab being a thin partition having a uniform thickness;
- said shell having concave external sides;
- said proximal end being outwardly curved; and,
- said internal cavity shaped and dimensioned to receive the thumb and at least one finger of the person with said tab disposed between the thumb and the at least one finger of the person.

15. The wipe according to claim 1, further including:
- said shell fabricated from paper.

* * * * *